US010748447B2

(12) United States Patent
Matthews et al.

(10) Patent No.: US 10,748,447 B2
(45) Date of Patent: Aug. 18, 2020

(54) SYSTEMS AND METHODS PROVIDING A COMPUTERIZED EYEWEAR DEVICE TO AID IN WELDING

(71) Applicant: Lincoln Global, Inc., City of Industry, CA (US)

(72) Inventors: William T. Matthews, Chesterland, OH (US); Joseph A. Daniel, Sagamore Hills, OH (US)

(73) Assignee: LINCOLN GLOBAL, INC., City of Industry, CA (US)

( * ) Notice: Subject to any disclaimer, the term of this patent is extended or adjusted under 35 U.S.C. 154(b) by 1045 days.

(21) Appl. No.: 14/105,758

(22) Filed: Dec. 13, 2013

(65) Prior Publication Data

US 2014/0346158 A1    Nov. 27, 2014

Related U.S. Application Data

(60) Provisional application No. 61/827,248, filed on May 24, 2013.

(51) Int. Cl.
*G09B 19/24* (2006.01)
*A61F 9/06* (2006.01)
(Continued)

(52) U.S. Cl.
CPC ............... *G09B 19/24* (2013.01); *A61F 9/06* (2013.01); *B23K 9/0953* (2013.01); *B23K 9/0956* (2013.01); *B23K 9/10* (2013.01); *B23K 9/1006* (2013.01); *B23K 9/32* (2013.01); *B23K 9/321* (2013.01); *B23K 37/00* (2013.01); *G02B 27/017* (2013.01); *G02B 27/0172* (2013.01);
(Continued)

(58) Field of Classification Search
CPC . A61F 9/06; A61F 9/025; A42B 3/225; A42B 3/145; A42B 3/14
USPC ........................ 345/8; 219/130.01, 147; 2/8.2
See application file for complete search history.

(56) References Cited

U.S. PATENT DOCUMENTS

| 1,159,119 | A | 11/1915 | Springer |
| D140,630 | S | 3/1945 | Garibay |

(Continued)

FOREIGN PATENT DOCUMENTS

| CA | 2698078 | 9/2011 |
| CN | 201083660 Y | 7/2008 |

(Continued)

OTHER PUBLICATIONS

Chuansong Wu: "Microcomputer-based welder training simulator", Computers in Industry, vol. 20, No. 3, Oct. 1992, pp. 321-325, XP000205597, Elsevier Science Publishers, Amsterdam, NL.

(Continued)

*Primary Examiner* — Tu B Hoang
*Assistant Examiner* — Thomas J Ward

(57) ABSTRACT

Systems and methods to aid a welder or welding student. A system may provide a real-world arc welding system or a virtual reality arc welding system along with a computerized eyewear device having a head-up display (HUD). The computerized eyewear device may be worn by a user under a conventional welding helmet as eye glasses are worn and may wirelessly communicate with a welding power source of a real-world arc welding system or a programmable processor-based subsystem of a virtual reality arc welding system.

12 Claims, 3 Drawing Sheets

(51) Int. Cl.

| | |
|---|---|
| *G02B 27/01* | (2006.01) |
| *B23K 9/095* | (2006.01) |
| *B23K 9/32* | (2006.01) |
| *B23K 9/10* | (2006.01) |
| *G09B 5/02* | (2006.01) |
| *B23K 37/00* | (2006.01) |
| *G09B 9/00* | (2006.01) |
| *G06K 9/00* | (2006.01) |
| *G09B 19/00* | (2006.01) |
| *G06F 3/0488* | (2013.01) |
| *G06F 3/16* | (2006.01) |

(52) U.S. Cl.
CPC ..... *G02B 27/0176* (2013.01); *G06K 9/00671* (2013.01); *G09B 5/02* (2013.01); *G09B 9/00* (2013.01); *G09B 19/003* (2013.01); *G02B 2027/014* (2013.01); *G02B 2027/0138* (2013.01); *G02B 2027/0158* (2013.01); *G02B 2027/0178* (2013.01); *G02B 2027/0187* (2013.01); *G06F 3/04883* (2013.01); *G06F 3/167* (2013.01)

(56) References Cited

U.S. PATENT DOCUMENTS

| | | |
|---|---|---|
| D142,377 S | 9/1945 | Dunn |
| D152,049 S | 12/1948 | Welch |
| 2,681,969 A | 6/1954 | Burke |
| D174,208 S | 3/1955 | Abidgaard |
| 2,728,838 A | 12/1955 | Barnes |
| D176,942 S | 2/1956 | Cross |
| 2,894,086 A | 7/1959 | Rizer |
| 3,035,155 A | 5/1962 | Hawk |
| 3,059,519 A | 10/1962 | Stanton |
| 3,356,823 A | 12/1967 | Waters et al. |
| 3,555,239 A | 1/1971 | Kerth |
| 3,621,177 A | 11/1971 | McPherson et al. |
| 3,654,421 A | 4/1972 | Streetman et al. |
| 3,739,140 A | 6/1973 | Rotilio |
| 3,866,011 A | 2/1975 | Cole |
| 3,867,769 A | 2/1975 | Schow et al. |
| 3,904,845 A | 9/1975 | Minkiewicz |
| 3,988,913 A | 11/1976 | Metcalfe et al. |
| D243,459 S | 2/1977 | Bliss |
| 4,024,371 A | 5/1977 | Drake |
| 4,041,615 A | 8/1977 | Whitehill |
| D247,421 S | 3/1978 | Driscoll |
| 4,124,944 A | 11/1978 | Blair |
| 4,132,014 A | 1/1979 | Schow |
| 4,237,365 A | 12/1980 | Lambros et al. |
| 4,280,041 A | 7/1981 | Kiessliing et al. |
| 4,280,137 A | 7/1981 | Ashida et al. |
| 4,314,125 A | 2/1982 | Nakamura |
| 4,359,622 A | 11/1982 | Dostoomian et al. |
| 4,375,026 A | 2/1983 | Kearney |
| 4,410,787 A | 10/1983 | Kremers et al. |
| 4,429,266 A | 1/1984 | Traadt |
| 4,452,589 A | 6/1984 | Denison |
| D275,292 S | 8/1984 | Bouman |
| D277,761 S | 2/1985 | Korovin et al. |
| D280,329 S | 8/1985 | Bouman |
| 4,611,111 A | 9/1986 | Baheti et al. |
| 4,616,326 A | 10/1986 | Meier et al. |
| 4,629,860 A | 12/1986 | Lindbom |
| 4,677,277 A | 6/1987 | Cook et al. |
| 4,680,014 A | 7/1987 | Paton et al. |
| 4,689,021 A | 8/1987 | Vasiliev et al. |
| 4,707,582 A | 11/1987 | Beyer |
| 4,716,273 A | 12/1987 | Paton et al. |
| D297,704 S | 9/1988 | Bulow |
| 4,867,685 A | 9/1989 | Brush et al. |
| 4,877,940 A | 10/1989 | Bangs et al. |
| 4,897,521 A | 1/1990 | Burr |
| 4,907,973 A | 3/1990 | Hon |
| 4,931,018 A | 6/1990 | Herbst et al. |
| 4,998,050 A | 3/1991 | Nishiyama et al. |
| 5,034,593 A | 7/1991 | Rice et al. |
| 5,061,841 A | 10/1991 | Richardson |
| 5,089,914 A | 2/1992 | Prescott |
| 5,192,845 A | 3/1993 | Kirmsse et al. |
| 5,206,472 A | 4/1993 | Myking et al. |
| 5,266,930 A | 11/1993 | Ichikawa et al. |
| 5,285,916 A | 2/1994 | Ross |
| 5,305,183 A | 4/1994 | Teynor |
| 5,320,538 A | 6/1994 | Baum |
| 5,337,611 A | 8/1994 | Fleming et al. |
| 5,360,156 A | 11/1994 | Ishizaka et al. |
| 5,360,960 A | 11/1994 | Shirk |
| 5,370,071 A | 12/1994 | Ackermann |
| D359,296 S | 6/1995 | Witherspoon |
| 5,424,634 A | 6/1995 | Goldfarb et al. |
| 5,436,638 A | 7/1995 | Bolas et al. |
| 5,464,957 A | 11/1995 | Kidwell et al. |
| D365,583 S | 12/1995 | Viken |
| 5,562,843 A | 10/1996 | Yasumoto |
| 5,670,071 A | 9/1997 | Ueyama et al. |
| 5,676,503 A | 10/1997 | Lang |
| 5,676,867 A | 10/1997 | Allen |
| 5,708,253 A | 1/1998 | Bloch et al. |
| 5,710,405 A | 1/1998 | Solomon et al. |
| 5,719,369 A | 2/1998 | White et al. |
| D392,534 S | 3/1998 | Degen et al. |
| 5,728,991 A | 3/1998 | Takada et al. |
| 5,751,258 A | 5/1998 | Fergason et al. |
| D395,296 S | 6/1998 | Kaye et al. |
| D396,238 S | 7/1998 | Schmitt |
| 5,781,258 A | 7/1998 | Debral et al. |
| 5,823,785 A | 10/1998 | Matherne, Jr. |
| 5,835,077 A | 11/1998 | Dao et al. |
| 5,835,277 A | 11/1998 | Hegg |
| 5,845,053 A | 12/1998 | Watanabe et al. |
| 5,963,891 A | 10/1999 | Walker et al. |
| 6,008,470 A | 12/1999 | Zhang et al. |
| 6,049,059 A | 4/2000 | Kim |
| 6,051,805 A | 4/2000 | Vaidya et al. |
| 6,114,645 A | 9/2000 | Burgess |
| 6,155,475 A | 12/2000 | Ekelof et al. |
| 6,155,928 A | 12/2000 | Burdick |
| 6,230,327 B1 | 5/2001 | Briand et al. |
| 6,236,013 B1 | 5/2001 | Delzenne |
| 6,236,017 B1 | 5/2001 | Smartt et al. |
| 6,242,711 B1 | 6/2001 | Cooper |
| 6,271,500 B1 | 8/2001 | Hirayama et al. |
| 6,330,938 B1 | 12/2001 | Nerve et al. |
| 6,330,966 B1 | 12/2001 | Eissfeller |
| 6,331,848 B1 | 12/2001 | Stove et al. |
| D456,428 S | 4/2002 | Aronson et al. |
| 6,373,465 B2 | 4/2002 | Jolly et al. |
| D456,828 S | 5/2002 | Aronson et al. |
| D461,383 S | 8/2002 | Balckburn |
| 6,441,342 B1 | 8/2002 | Hsu |
| 6,445,964 B1 | 9/2002 | White et al. |
| 6,492,618 B1 | 12/2002 | Flood et al. |
| 6,506,997 B2 | 1/2003 | Matsuyama |
| 6,552,303 B1 | 4/2003 | Blankenship et al. |
| 6,560,029 B1 | 5/2003 | Dobbie et al. |
| 6,563,489 B1 | 5/2003 | Latypov et al. |
| 6,568,846 B1 | 5/2003 | Cote et al. |
| D475,726 S | 6/2003 | Suga et al. |
| 6,572,379 B1 | 6/2003 | Sears et al. |
| 6,583,386 B1 | 6/2003 | Ivkovich |
| 6,621,049 B2 | 9/2003 | Suzuki |
| 6,624,388 B1 | 9/2003 | Blankenship et al. |
| D482,171 S | 11/2003 | Vui et al. |
| 6,647,288 B2 | 11/2003 | Madill et al. |
| 6,649,858 B2 | 11/2003 | Wakeman |
| 6,655,645 B1 | 12/2003 | Lu et al. |
| 6,660,965 B2 | 12/2003 | Simpson |
| 6,697,701 B2 | 2/2004 | Hillen et al. |
| 6,697,770 B1 | 2/2004 | Nagetgaal |
| 6,703,585 B2 | 3/2004 | Suzuki |
| 6,708,385 B1 | 3/2004 | Lemelson |

(56) References Cited

U.S. PATENT DOCUMENTS

| | | | |
|---|---|---|---|
| 6,710,298 B2 * | 3/2004 | Eriksson | A61F 9/06 219/130.01 |
| 6,710,299 B2 | 3/2004 | Blankenship et al. | |
| 6,715,502 B1 | 4/2004 | Rome et al. | |
| D490,347 S | 5/2004 | Meyers | |
| 6,730,875 B2 | 5/2004 | Hsu | |
| 6,734,393 B1 * | 5/2004 | Friedl | A61F 9/067 219/130.01 |
| 6,744,011 B1 | 6/2004 | Hu et al. | |
| 6,750,428 B2 | 6/2004 | Okamoto et al. | |
| 6,772,802 B2 | 8/2004 | Few | |
| 6,788,442 B1 | 9/2004 | Potin et al. | |
| 6,795,778 B2 | 9/2004 | Dodge et al. | |
| 6,798,974 B1 | 9/2004 | Nakano et al. | |
| 6,857,553 B1 | 2/2005 | Hartman et al. | |
| 6,858,817 B2 | 2/2005 | Blankenship et al. | |
| 6,865,926 B2 | 3/2005 | O'Brien et al. | |
| D504,449 S | 4/2005 | Butchko | |
| 6,920,371 B2 | 7/2005 | Hillen et al. | |
| 6,940,039 B2 | 9/2005 | Blankenship et al. | |
| 7,021,937 B2 | 4/2006 | Simpson et al. | |
| 7,126,078 B2 | 10/2006 | Demers et al. | |
| 7,132,617 B2 | 11/2006 | Lee et al. | |
| 7,170,032 B2 | 1/2007 | Flood | |
| 7,194,447 B2 | 3/2007 | Harvey et al. | |
| 7,247,814 B2 | 7/2007 | Ott | |
| D555,446 S | 11/2007 | Picaza Ibarrondo | |
| 7,315,241 B1 | 1/2008 | Daily et al. | |
| D561,973 S | 2/2008 | Kinsley et al. | |
| 7,353,715 B2 | 4/2008 | Myers | |
| 7,363,137 B2 | 4/2008 | Brant et al. | |
| 7,375,304 B2 | 5/2008 | Kainec et al. | |
| 7,381,923 B2 | 6/2008 | Gordon et al. | |
| 7,414,595 B1 | 8/2008 | Muffler | |
| 7,465,230 B2 | 12/2008 | LeMay et al. | |
| 7,478,108 B2 | 1/2009 | Townsend et al. | |
| D587,975 S | 3/2009 | Aronson et al. | |
| 7,516,022 B2 | 4/2009 | Lee et al. | |
| D602,057 S | 10/2009 | Osicki | |
| 7,621,171 B2 | 11/2009 | O'Brien | |
| D606,102 S | 12/2009 | Bender et al. | |
| 7,631,968 B1 | 12/2009 | Dobson | |
| 7,643,890 B1 | 1/2010 | Hillen et al. | |
| 7,687,741 B2 | 3/2010 | Kainec et al. | |
| D614,217 S | 4/2010 | Peters et al. | |
| D615,573 S | 5/2010 | Peters et al. | |
| 7,817,162 B2 | 10/2010 | Bolick et al. | |
| 7,853,645 B2 | 12/2010 | Brown et al. | |
| D631,074 S | 1/2011 | Peters et al. | |
| 7,874,921 B2 | 1/2011 | Baszucki et al. | |
| 7,962,967 B2 | 6/2011 | Becker | |
| 7,970,172 B1 | 6/2011 | Hendrickson | |
| 7,972,129 B2 | 7/2011 | O'Donoghue | |
| 7,991,587 B2 | 8/2011 | Ihn | |
| 8,069,017 B2 | 11/2011 | Hallquist | |
| 8,224,881 B1 | 7/2012 | Spear et al. | |
| 8,248,324 B2 | 8/2012 | Nangle | |
| 8,265,886 B2 | 9/2012 | Bisiaux et al. | |
| 8,274,013 B2 | 9/2012 | Wallace | |
| 8,287,522 B2 | 10/2012 | Moses et al. | |
| 8,316,462 B2 | 11/2012 | Becker et al. | |
| 8,363,048 B2 | 1/2013 | Gering | |
| 8,365,603 B2 | 2/2013 | Lesage et al. | |
| 8,512,043 B2 | 8/2013 | Choquet | |
| 8,569,646 B2 | 10/2013 | Daniel et al. | |
| 8,777,629 B2 | 7/2014 | Kreindl et al. | |
| 9,073,138 B2 | 7/2015 | Wills | |
| 9,352,411 B2 * | 5/2016 | Batzler | B23K 9/32 |
| 2001/0045808 A1 | 11/2001 | Hietmann et al. | |
| 2001/0052893 A1 | 12/2001 | Jolly et al. | |
| 2002/0032553 A1 | 3/2002 | Simpson et al. | |
| 2002/0046999 A1 | 4/2002 | Veikkolainen et al. | |
| 2002/0050984 A1 | 5/2002 | Roberts | |
| 2002/0085843 A1 | 7/2002 | Mann | |
| 2002/0175897 A1 | 11/2002 | Pelosi | |
| 2003/0000931 A1 | 1/2003 | Ueda et al. | |
| 2003/0023592 A1 | 1/2003 | Modica et al. | |
| 2003/0025884 A1 | 2/2003 | Hamana et al. | |
| 2003/0106787 A1 | 6/2003 | Santilli | |
| 2003/0111451 A1 | 7/2003 | Blankenship et al. | |
| 2003/0172032 A1 | 9/2003 | Choquet | |
| 2003/0234885 A1 | 12/2003 | Pilu | |
| 2004/0020907 A1 | 2/2004 | Zauner et al. | |
| 2004/0035990 A1 | 2/2004 | Ackeret | |
| 2004/0050824 A1 | 3/2004 | Samler | |
| 2004/0140301 A1 | 7/2004 | Blankenship et al. | |
| 2005/0007504 A1 | 1/2005 | Fergason | |
| 2005/0017152 A1 | 1/2005 | Fergason | |
| 2005/0046584 A1 | 3/2005 | Breed | |
| 2005/0050168 A1 | 3/2005 | Wen | |
| 2005/0101767 A1 | 5/2005 | Clapham et al. | |
| 2005/0103766 A1 | 5/2005 | Iizuka et al. | |
| 2005/0103767 A1 | 5/2005 | Kainec et al. | |
| 2005/0109735 A1 | 5/2005 | Flood | |
| 2005/0128186 A1 | 6/2005 | Shahoian et al. | |
| 2005/0133488 A1 | 7/2005 | Blankenship | |
| 2005/0159840 A1 | 7/2005 | Lin et al. | |
| 2005/0189336 A1 | 9/2005 | Ku | |
| 2005/0199602 A1 | 9/2005 | Kaddani et al. | |
| 2005/0230573 A1 | 10/2005 | Ligertwood | |
| 2005/0252897 A1 | 11/2005 | Hsu | |
| 2005/0275913 A1 | 12/2005 | Vesely et al. | |
| 2005/0275914 A1 | 12/2005 | Vesely et al. | |
| 2006/0014130 A1 | 1/2006 | Weinstein | |
| 2006/0136183 A1 | 6/2006 | Choquet | |
| 2006/0163227 A1 | 7/2006 | Hillen et al. | |
| 2006/0169682 A1 | 8/2006 | Kainec et al. | |
| 2006/0173619 A1 | 8/2006 | Brant et al. | |
| 2006/0189260 A1 | 8/2006 | Sung | |
| 2006/0207980 A1 | 9/2006 | Jacovetty et al. | |
| 2006/0213892 A1 | 9/2006 | Ott | |
| 2006/0214924 A1 | 9/2006 | Kawamoto et al. | |
| 2006/0226137 A1 | 10/2006 | Huismann et al. | |
| 2006/0252543 A1 | 11/2006 | Van Noland et al. | |
| 2006/0258447 A1 | 11/2006 | Baszucki et al. | |
| 2007/0034611 A1 | 2/2007 | Drius et al. | |
| 2007/0038400 A1 | 2/2007 | Lee et al. | |
| 2007/0045488 A1 | 3/2007 | Shin | |
| 2007/0088536 A1 | 4/2007 | Ishikawa | |
| 2007/0112889 A1 | 5/2007 | Cook et al. | |
| 2007/0198117 A1 | 8/2007 | Wajihuddin | |
| 2007/0211026 A1 | 9/2007 | Ohta | |
| 2007/0221797 A1 | 9/2007 | Thompson et al. | |
| 2007/0256503 A1 | 11/2007 | Wong et al. | |
| 2007/0277611 A1 | 12/2007 | Portzgen et al. | |
| 2007/0291035 A1 | 12/2007 | Vesely et al. | |
| 2008/0031774 A1 | 2/2008 | Magnant et al. | |
| 2008/0038702 A1 | 2/2008 | Choquet | |
| 2008/0078811 A1 | 4/2008 | Hillen et al. | |
| 2008/0078812 A1 | 4/2008 | Peters et al. | |
| 2008/0117203 A1 | 5/2008 | Gering | |
| 2008/0128398 A1 | 6/2008 | Schneider | |
| 2008/0135533 A1 | 6/2008 | Ertmer et al. | |
| 2008/0140815 A1 | 7/2008 | Brant et al. | |
| 2008/0149686 A1 | 7/2008 | Daniel et al. | |
| 2008/0203075 A1 | 8/2008 | Feldhausen et al. | |
| 2008/0233550 A1 | 9/2008 | Solomon | |
| 2008/0314887 A1 | 12/2008 | Stoger et al. | |
| 2009/0015585 A1 | 1/2009 | Klusza | |
| 2009/0021514 A1 | 1/2009 | Klusza | |
| 2009/0045183 A1 | 2/2009 | Artelsmair et al. | |
| 2009/0057286 A1 | 3/2009 | Ihara et al. | |
| 2009/0152251 A1 | 6/2009 | Dantinne et al. | |
| 2009/0173726 A1 | 7/2009 | Davidson et al. | |
| 2009/0184098 A1 | 7/2009 | Daniel et al. | |
| 2009/0200281 A1 | 8/2009 | Hampton | |
| 2009/0200282 A1 | 8/2009 | Hampton | |
| 2009/0231423 A1 | 9/2009 | Becker | |
| 2009/0259444 A1 | 10/2009 | Dolansky et al. | |
| 2009/0298024 A1 | 12/2009 | Batzler et al. | |
| 2009/0325699 A1 | 12/2009 | Delgiannidis | |
| 2010/0012017 A1 | 1/2010 | Miller | |
| 2010/0012637 A1 | 1/2010 | Jaeger | |
| 2010/0048273 A1 | 2/2010 | Wallace et al. | |

(56) References Cited

U.S. PATENT DOCUMENTS

| | | | |
|---|---|---|---|
| 2010/0062405 A1 | 3/2010 | Zboray et al. | |
| 2010/0062406 A1* | 3/2010 | Zboray | G09B 19/24 434/234 |
| 2010/0096373 A1 | 4/2010 | Hillen et al. | |
| 2010/0121472 A1 | 5/2010 | Babu et al. | |
| 2010/0133247 A1 | 6/2010 | Mazumder et al. | |
| 2010/0133250 A1 | 6/2010 | Sardy et al. | |
| 2010/0176107 A1 | 7/2010 | Bong | |
| 2010/0201803 A1 | 8/2010 | Melikian | |
| 2010/0223706 A1* | 9/2010 | Becker | A42B 3/30 2/8.2 |
| 2010/0224610 A1 | 9/2010 | Wallace | |
| 2010/0276396 A1 | 11/2010 | Cooper et al. | |
| 2010/0299101 A1 | 11/2010 | Shimada et al. | |
| 2010/0307249 A1 | 12/2010 | Lesage et al. | |
| 2011/0006047 A1 | 1/2011 | Penrod et al. | |
| 2011/0060568 A1 | 3/2011 | Goldfine et al. | |
| 2011/0091846 A1 | 4/2011 | Kreindl et al. | |
| 2011/0114615 A1 | 5/2011 | Daniel et al. | |
| 2011/0116076 A1 | 5/2011 | Chantry et al. | |
| 2011/0117527 A1 | 5/2011 | Conrardy et al. | |
| 2011/0122495 A1 | 5/2011 | Togashi | |
| 2011/0183304 A1 | 7/2011 | Wallace et al. | |
| 2011/0248864 A1 | 10/2011 | Becker et al. | |
| 2011/0316516 A1 | 12/2011 | Schiefermuller et al. | |
| 2012/0189993 A1 | 7/2012 | Kindig et al. | |
| 2012/0291172 A1 | 11/2012 | Wills et al. | |
| 2012/0298640 A1 | 11/2012 | Conrardy et al. | |
| 2013/0026150 A1 | 1/2013 | Chantry et al. | |
| 2013/0040270 A1 | 2/2013 | Albrecht | |
| 2013/0044042 A1* | 2/2013 | Olsson | G02B 27/0176 345/8 |
| 2013/0075380 A1 | 3/2013 | Albrech et al. | |
| 2013/0189657 A1 | 7/2013 | Wallace et al. | |
| 2013/0189658 A1 | 7/2013 | Peters et al. | |
| 2013/0206741 A1* | 8/2013 | Pfeifer | B23K 9/095 219/130.01 |
| 2014/0038143 A1 | 2/2014 | Daniel et al. | |
| 2014/0134580 A1 | 5/2014 | Becker | |
| 2014/0263224 A1 | 9/2014 | Becker | |
| 2014/0272836 A1 | 9/2014 | Becker | |
| 2014/0272837 A1 | 9/2014 | Becker | |
| 2014/0272838 A1 | 9/2014 | Becker | |
| 2015/0056584 A1 | 2/2015 | Boulware et al. | |
| 2015/0056585 A1 | 2/2015 | Boulware et al. | |
| 2015/0056586 A1 | 2/2015 | Penrod et al. | |

FOREIGN PATENT DOCUMENTS

| | | |
|---|---|---|
| CN | 101419755 A1 | 4/2009 |
| CN | 201229711 Y | 4/2009 |
| CN | 101571887 A | 11/2009 |
| CN | 101587659 A | 11/2009 |
| CN | 102165504 | 8/2011 |
| CN | 103871279 A | 6/2014 |
| CN | 105209207 | 12/2015 |
| DE | 28 33 638 A1 | 2/1980 |
| DE | 30 46 634 A1 | 1/1984 |
| DE | 32 44 307 A1 | 5/1984 |
| DE | 35 22 581 A1 | 1/1987 |
| DE | 4037879 A1 | 6/1991 |
| DE | 196 15 069 A1 | 10/1997 |
| DE | 197 39 720 C1 | 10/1998 |
| DE | 19834205 A1 | 2/2000 |
| DE | 200 09 543 U1 | 8/2001 |
| DE | 10 2005 047 204 A1 | 4/2007 |
| DE | 10 2010 038 902 A1 | 2/2012 |
| DE | 202012013151 U1 | 2/2015 |
| EP | 0 108 599 A1 | 5/1984 |
| EP | 0 127 299 | 12/1984 |
| EP | 0 145 891 A1 | 6/1985 |
| EP | 319623 B1 | 10/1990 |
| EP | 0852986 A1 | 7/1998 |
| EP | 1010490 | 6/2000 |
| EP | 1 527 852 A1 | 5/2005 |
| EP | 1905533 A2 | 4/2008 |
| ES | 2 274 736 A1 | 5/2007 |
| ES | 2274736 A1 | 5/2007 |
| FR | 1456780 | 3/1965 |
| FR | 2 827 066 A1 | 1/2003 |
| FR | 2 926 660 A1 | 7/2009 |
| GB | 1 455 972 | 11/1976 |
| GB | 1 511 608 | 5/1978 |
| GB | 2 254 172 A | 9/1992 |
| GB | 2435838 A | 9/2007 |
| GB | 2 454 232 A | 5/2009 |
| GB | 2454232 | 6/2009 |
| JP | 2-224877 | 9/1990 |
| JP | 05-329645 | 12/1993 |
| JP | 07-047471 | 2/1995 |
| JP | 07-232270 | 9/1995 |
| JP | 08-505091 | 4/1996 |
| JP | 08-150476 | 6/1996 |
| JP | 08-132274 | 5/1998 |
| JP | 2000237872 | 5/2000 |
| JP | 2000-167666 A | 6/2000 |
| JP | 2001-071140 A | 3/2001 |
| JP | 2002278670 A | 9/2002 |
| JP | 2003-200372 A | 7/2003 |
| JP | 2003240562 | 8/2003 |
| JP | 2003-326362 A | 11/2003 |
| JP | 2006-006604 A | 1/2006 |
| JP | 2006-281270 A | 10/2006 |
| JP | 2007-290025 A | 11/2007 |
| JP | 2009-500178 A | 1/2009 |
| JP | 2009160636 A | 7/2009 |
| JP | 2310019646 | 1/2010 |
| JP | 2012024867 A | 2/2012 |
| JP | 2013504437 | 2/2013 |
| KR | 20090010693 | 1/2009 |
| RU | 2008 108 601 C1 | 11/2009 |
| SU | 1038963 A1 | 8/1983 |
| WO | 98/45078 | 10/1998 |
| WO | 0112376 A1 | 2/2001 |
| WO | 01/43910 | 6/2001 |
| WO | 0158400 A1 | 8/2001 |
| WO | 2006034571 A1 | 4/2006 |
| WO | 2009120921 | 1/2009 |
| WO | 2009060231 A1 | 5/2009 |
| WO | 2009149740 A1 | 12/2009 |
| WO | 2010000003 A2 | 1/2010 |
| WO | 2010044982 | 4/2010 |
| WO | 2010091493 A1 | 8/2010 |
| WO | 2011045654 A1 | 4/2011 |
| WO | 2011058433 | 5/2011 |
| WO | 2011058433 A1 | 5/2011 |
| WO | 2011067447 A1 | 6/2011 |
| WO | 2011/097035 | 8/2011 |
| WO | 2011097035 A2 | 8/2011 |
| WO | 2012082105 A1 | 6/2012 |
| WO | 2012143327 A1 | 10/2012 |
| WO | 20121327060 | 10/2012 |
| WO | 2013014202 A1 | 1/2013 |
| WO | 2013025672 | 2/2013 |
| WO | 2013114189 A1 | 8/2013 |
| WO | 2013175079 A1 | 11/2013 |
| WO | 2014007830 A1 | 1/2014 |
| WO | 2014019045 A1 | 2/2014 |
| WO | 2014020386 | 2/2014 |
| WO | 2014140682 | 9/2014 |

OTHER PUBLICATIONS

SIMFOR / CESOL, "RV-SOLD" Welding Simulator, Technical and Functional Features, 20 pages, no date available.

International Search Report for PCT/IB2009/00605.

"Design and Implementation of a Video Sensor for Closed Loop Control of Back Bead Weld Puddle Width," Robert Schoder, Massachusetts, Institute of Technology, Dept. of Mechanical Engineering, May 27, 1983.

Hills and Steele, Jr.; "Data Parallel Algorithms", Communications of the ACM, Dec. 1986, vol. 29, No. 12, p. 1170.

(56) References Cited

OTHER PUBLICATIONS

Russell and Norvig, "Artificial Intelligence: A Modern Approach", Prentice-Hall (Copywrite 1995).
Mechanisms and Mechanical Devices Source Book, Chironis, Neil Sclater; McGraw Hill; 2nd Addition, 1996.
ARS Electronica Linz GmbH, Fronius, 2 pages, May 18, 1997.
"Penetration in Spot GTA Welds during Centrifugation, "D.K. Aidun and S.A. Martin; Journal of Material Engineering and Performance vol. 7(5) Oct. 1998—597.
Arc+ simulator; httl://www.123arc.com/en/depliant_ang.pdf; 2000.
Wade, "Human uses of ultrasound: ancient and modern", Ulrasonics vol. 38, dated 2000.
ASME Definitions, Consumables, Welding Positions, dated Mar. 19, 2001. See http://www.gowelding.com/asme4.htm.
Code Aster (Software) EDF (France), Oct. 2001.
"The influence of fluid flow phenomena on the laser beam welding process"; International Journal of Heat and Fluid Flow 23, dated 2002.
The Lindoln Electric Company; CheckPoint Production Monitoring brochure; four (4) pages; http://www.lincolnelectric.com/assets/en_US/products/literature/s232.pdf; Publication 82.32; Issue Date Feb. 2012.
"Numerical Analysis of Metal Transfer in Gas Metal Arc Welding," G. Wang, P.G. Huang, and Y.M. Zhang. Departments of Mechanical and Electrical Engineering. University of Kentucky, Dec. 10, 2001.
Desroches, X.; Code-Aster, Note of use for aciculations of welding; Instruction manual U2.03 booklet: Thermomechincal; Document: U2.03.05; Oct. 1, 2003.
Fast, K. et al., "Virtual Training for Welding", Mixed and Augmented Reality, 2004, ISMAR 2004, Third IEEE and SM International Symposium on Arlington, VA, Nov. 2-5, 2004.
Cooperative Research Program, Virtual Reality Welder Training, Summary Report SR 0512, 4 pages, Jul. 2005.
Porter, et al., Virtual Reality Training, Paper No. 2005-P19, 14 pages, 2005.
Eduwelding+, Weld Into the Future; Online Welding Seminar—A virtual training environment; 123arc.com; 4 pages, 2005.
Miller Electric Mfg Co.; MIG Welding System features weld monitoring software; NewsRoom 2010 (Dialog® File 992); © 2011 Dialog. 2010; http://www.dialogweb.com/cgi/dwclient?reg=133233430487; three (3) pages; printed Mar. 8, 2012.
Numerical simulation to study the effect of tack welds and root gap on welding deformations and residual stresses of a pipe-flange joint by M. Abida and M. Siddique, Faculty of Mechanical Engineering, GIK Institute of Engineering Sciences and Technology, Topi, NWFP, Pakistan. Available on-line Aug. 25, 2005.
Abbas, M. et. al.; Code_Aster; Introduction to Code_Aster; User Manual; Booklet U1.0—: Introduction to Code_Aster; Document: U1.02.00; Version 7.4; Jul. 22, 2005.
Mavrikios D et al, A prototype virtual reality-based demonstrator for immersive and interactive simulation of welding processes, International Journal of Computer Integrated manufacturing, Taylor and Francis, Basingstoke, GB, vol. 19, No. 3, Apr. 1, 2006, pp. 294-300.
Virtual Reality Welder Trainer, Sessiion 5: Joining Technologies for Naval Applications: earliest date Jul. 14, 2006 (http://weayback.archive.org) by Nancy C. Porter, Edision Welding Institute; J. Allan Cote, General Dynamics Electric Boat; Timothy D. Gifford, VRSim, and Wim Lam, FCS Controls.
16th International Shop and Offshore Structures Congress: Aug. 20-25, 2006: Southhampton, UK, vol. 2 Specialist Committee V.3 Fabrication Technology Committee Mandate: T Borzecki, G. Bruce, Y.S. Han, M. Heinemann, A Imakita, L. Josefson, W. Nie, D. Olson, F. Roland, and Y. Takeda.
Ratnam and Khalid: "Automatic classification of weld defects using simulated data and an MLP neutral network." Insight vol. 49, No. 3; Mar. 2007.
Wang et al., Study on welder training by means of haptic guidance and virtual reality for arc welding, 2006 IEEE International Conference on Robotics and Biomimetics, ROBIO 2006 ISBN-10: 1424405718, p. 954-958.

CS Wave, The Virtual Welding Trainer, 6 pages, 2007.
asciencetutor.com, A division of Advanced Science and Automation Corp., VWL (Virtual Welding Lab), 2 pages, 2007.
Eric Linholm, John Nickolls, Stuart Oberman, and John Montrym, "NVIDIA Testla: A Unifired Graphics and Computing Architecture", IEEE Computer Society, 2008.
NSRP ASE, Low-Cost Virtual Realtiy Welder Training System, 1 Page, 2008.
Edison Welding Institute, E-Weld Predictor, 3 pages, 2008.
CS Wave, A Virtual learning tool for welding motion, 10 pages, Mar. 14, 2008.
The Fabricator, Virtual Welding, 4 pages, Mar. 2008.
N. A. Tech., P/NA.3 Process Modeling and Optimization, 11 pages, Jun. 4, 2008.
FH Joanneum, Fronius—virtual welding, 2 pages, May 12, 2008.
Eduwelding+, Training Activities with arc+ simulator; Weld Into the Future, Online Welding Simulator—A virtual training environment; 123arc.com; 6 pages, May 2008.
ChemWeb.com, Journal of Materials Engineering and Performance (v.7, #5), 3 pgs., printed Sep. 26, 2012.
Choquet, Claude; "ARC+: Today's Virtual Reality Solution for Welders" Internet Page, Jan. 1, 2008.
Juan Vicenete Rosell Gonzales, "RV-Sold: simulator virtual para la formacion de soldadores"; Deformacion Metalica, Es. vol. 34, No. 301 Jan. 1, 2008.
White et al., Virtual welder training, 2009 IEEE Virtual Reality Conference, p. 303, 2009.
Training in a virtual environment gives welding students a leg up, retrieved on Apr. 12, 2010 from: http://www.thefabricator.com/article/arcwelding/virtually-welding.
SimWelder, retrieved on Apr. 12, 2010 from: http://www.simwelder.com.
P. Beatriz Garcia-Allende, Jesus Mirapeix, Olga M. Conde, Adolfo Cobo and Jose M. Lopez-Higuera; Defect Detection in Arc-Welding Processes by Means of the Line-to-Continuum Method and Feature Selection; www.mdpi.com/journal/sensors; Sensors 2009, 9, 7753-7770; doi; 10.3390/s91007753.
Production Monitoring 2 brochure, four (4) pages, The Lincoln Electric Company, May 2009.
International Search Report and Written Opinion from PCT/IB10/02913 dated Apr. 19, 2011.
Bjorn G. Agren; Sensor Integration for Robotic Arc Welding; 1995; vol. 5604C of Dissertations Abstracts International p. 1123; Dissertation Abs Online (Dialog® File 35): © 2012 ProQuest Info& Learning: http://dialogweb.com/cgi/dwclient?req=1331233317524; one (1) page; printed Mar. 8, 2012.
Heat and mass transfer in gas metal arc welding. Part 1: the arc by J. Hu and Hi Tsai found in ScienceDirect, International Journal of Heat and Mass Transfer 50 (2007) 833-846 Available on Line on Oct. 24, 2006 http://www.web.mst.edu/~tsai/publications/HU-IJHMT-2007-1-60.pdf.
Texture Mapping by M. Ian Graham, Carnegie Mellon University Class 15-462 Computer Graphics, Lecture 10 dated Feb. 13, 2003.
ViziTech USA, retrieved on Mar. 27, 2014 from http://vizitechusa.com/, 2 pages.
Guu and Rokhlin ,Technique for Simultaneous Real-Time Measurements of Weld Pool Surface Geometry and Arc Force, 10 pages, Dec. 1992.
D. Mavrikios, V. Karabatsou, D. Fragos and G. Chryssolouris, A prototype virtual reality-based demonstrator for immersive and interactive simulation of welding processes, International Journal of Computer Integrated Manufacturing, abstract, 1 page, Apr.-May 2006, 294-300, vol. 19, No. 3, http://eds.a.ebscohost.com/eds/pdfviewer/pdfviewer?vid=2&sid=ab8fe67b-1 f7.
S.B. Chen, L. Wu, Q. L. Wang and Y. C. Liu, Self-Learning Fuzzy Neural Networks and Computer Vision for Control of Pulsed GTAW, 9 pages, dated May 1997.
Patrick Rodjito, Position tracking and motion prediction using Fuzzy Logic, 81 pages, 2006, Colby College.
D'Huart, Deat, and Lium; Virtual Environment for Training, 6th International Conference, ITS 20002, 6 pages, Jun. 2002.

(56) References Cited

OTHER PUBLICATIONS

Konstantinos Nasios (Bsc), Improving Chemical Plant Safety Training Using Virtual Reality, Thesis submitted to the University of Nottingham for the Degree of Doctor of Philosophy, 313 pages, Dec. 2001.

Nancy C. Porter, J. Allan Cote, Timothy D. Gifford, and Wim Lam, Virtual Reality Welder Training, 29 pages, dated Jul. 14, 2006.

J.Y. (Yosh) Mantinband, Hillel Goldenberg, Llan Kleinberger, Paul Kleinberger, Autosteroscopic, field-sequential display with full freedom of movement Or Let the display were the shutter-glasses, 3ality (Israel) Ltd., 2002.

Echtler et al, "17 The Intelligent Welding Gun: Augmented Reality for Experimental Vehicle Construction," Virtual and Augmented Reality Applications in Manufacturing (2003) pp. 1-27.

Teeravarunyou et al, "Computer Based Welding Training System," International Journal of Industrial Engineering (2009) 16(2): 116-125.

Antonelli et al, "A Semi-Automated Welding Station Exploiting Human-Robot Interaction," Advanced Manufacturing Systems and Technology (2011) pp. 249-260.

Praxair Technology Inc, "The RealWeld Trainer System: Real Weld Training Under Real Conditions" Brochure (2013) 2 pages.

United States Provisional Patent Application for "System for Characterizing Manual Welding Operations on Pipe and Other Curved Structures," U.S. Appl. No. 62/055,724, filed Sep. 26, 2014, 35 pages.

Lincoln Global, Inc., "VRTEX 360: Virtual Reality Arc Welding Trainer" Brochure (2015) 4 pages.

Wuhan Onew Technology Co Ltd, "ONEW-360 Welding Training Simulator" http://en.onewtech.com/_d276479751.htm as accessed on Jul. 10, 2015, 12 pages.

The Lincoln Electric Company, "VRTEX Virtual Reality Arc Welding Trainer," http://www.lincolnelectric.com/en-us/equipment/training-equipment/Pages/vrtex.aspx as accessed on Jul. 10, 2015, 3 pages.

Miller Electric Mfg Co, "LiveArc: Welding Performance Management System" Owner's Manual, (Jul. 2014) 64 pages.

Miller Electric Mfg Co, "LiveArc Welding Performance Management System" Brochure, (Dec. 2014) 4 pages.

Steve Mann, Raymond Chun Bing Lo, Kalin Ovtcharov, Shixiang Gu, David Dai, Calvin Ngan, Tao Ai, Realtime HDR (High Dynamic Range) Video for Eyetap Wearable Computers, FPGS-Based Seeing Aids, and Glasseyes (Eyetaps), 2012 25th IEEE Canadian Conference on Electrical and Computer Engineering (CCECE),pp. 1-6, 6 pages, Apr. 29, 2012.

Kyt Dotson, Augmented Reality Welding Helmet Prototypes How Awsome the Technology Can Get, Sep. 26, 2012, Retrieved from the Internet: URL:http://siliconangle.com/blog/2012/09/26/augmented-reality-welding-helmet-prototypes-how-awesome-the-technology-can-get/,1 page, retrieved on Sep. 26, 2014.

Terrence O'Brien, "Google's Project Glass gets some more details",Jun. 27, 2012 (Jun. 27, 2012), Retrieved from the Internet: http://www.engadget.com/2012/06/27/googles-project-glass-gets-some-more-details/, 1 page, retrieved on Sep. 26, 2014.

Yao, et al., 'Development of a Robot System for Pipe Welding'. 2010 International Conference on Measuring echnology and Mechatronics Automation. Retrieved from the Internet: http://ieeexplore.ieee.org/stamp/stamp.jsp?tp=&arnumber=5460347&tag=1; pp. 1109-1112, 4 pages, 2010.

ANSI/A WS D 10.11 MID 10. 11 :2007 Guide for Root Pass Welding of Pipe without Backing Edition: 3rd American Welding Society / Oct. 13, 2006/36 pages ISBN: 0871716445, 6 pagess, 2007.

M. Jonsson, L. Karlsson, and L-E Lindgren, Simulation of Tack Welding Procedures in Butt Joint Welding of Plates Welding Research Supplement, 7 pages, Oct. 1985.

Isaac Brana Veiga, Simulation of a Work Cell in the IGRIP Program , 50 pages, dated 2006.

Balijepalli, A. and Kesavadas, Haptic Interfaces for Virtual Environment and Teleoperator Systems, Haptics 2003, 7-.,Department of Mechanical & Aerospace Engineering, State University of New York at Buffalo, NY, 7 pages, 2003.

Johannes Hirche, Alexander Ehlert, Stefan Guthe, Michael Doggett, Hardware Accelerated Per-Pixel Displacement Mapping, 8 pages.

William T. Reeves, "Particles Systems—A Technique for Modeling a Class of Fuzzy Objects", Computer Graphics 17:3 pp. 359-376, 17 pages, 1983.

T. Borzecki, G. Bruce, YS. Han, et al., Specialist Committee V.3 Fabrication Technology Committee Mandate, Aug. 20-25, 2006, 49 pages, vol. 2, 16th International Ship and Offshore Structures Congress, Southampton, UK.

G. Wang, P.G. Huang, and Y.M. Zhang: "Numerical Analysis of Metal Transfer in Gas Metal Arc Welding": Departments of Mechanical Engineering; and Electrical and Computer Engineering, University of Kentucky, Lexington, KY 40506-0108, Dec. 10, 2001, 10 pages.

ISMAR 2004 The Third IEEE and ACM International Symposium on Mixed and Augmented reality; Nov. 2-5, Arlington, VA, USA.

Kenneth Fast, et al.; National Shipbuilding Research Program (NSRP); Virtual Welding—a Low Cost Virtual Reality Welder Training System; Phase II Final Report Feb. 29, 2012.

The Application of Micro-computer in Robotic Technologies.

* cited by examiner

SYSTEMS AND METHODS PROVIDING A COMPUTERIZED EYEWEAR DEVICE TO AID IN WELDING

INCORPORATION BY REFERENCE

This U.S. patent application claims priority to and the benefit of U.S. provisional patent application Ser. No. 61/827,248 filed on May 24, 2013, which is incorporated herein by reference in its entirety. Published U.S. patent applications (US 2013/0044042) having application Ser. No. 13/212,686 and filed on Aug. 18, 2013 is incorporated by reference herein in its entirety. Published U.S. patent applications (US 2010/0062405) having application Ser. No. 12/501,257 and filed on Jul. 10, 2009 is incorporated by reference herein in its entirety.

TECHNICAL FIELD

Certain embodiments of the present invention relate to welding. More particularly, certain embodiments of the present invention relate to systems and methods providing visualization and communication capabilities to a welder using a welding system via a computerized eyewear device.

BACKGROUND

Providing information to a welding student in real time during a welding process (whether a real-world welding process or a simulated welding process) is important to aid the welding student in the learning process. Similarly, providing information to an expert welder in real time during a real-world welding process can aid the expert welder in the welding process. Furthermore, providing the ability for a welding student or an expert welder to easily communicate with (e.g., provide commands to) a welding system (real or simulated) can allow for a more efficient and user-friendly welding experience. Today, a welding helmet may be provided with simple light indicators representative of welding information which don't require a welder to be able to focus sharply on the light indicators, since the light indicators may be within one inch of the welder's eye. Simply being able to see that the color of a light indicator is red or green or yellow, for example, is provided. Thus, there is an ongoing need to improve how a welder or welding student interacts with a welding system and how information is provided and viewed in real time.

Further limitations and disadvantages of conventional, traditional, and proposed approaches will become apparent to one of skill in the art, through comparison of such systems and methods with embodiments of the present invention as set forth in the remainder of the present application with reference to the drawings.

SUMMARY

In one embodiment, a system is provided. The system includes a welding power source of an arc welding system and a computerized eyewear device having a head-up display (HUD). The computerized eyewear device is configured to be worn by a user as eye glasses are worn, while the user also wears a protective welding helmet. The computerized eyewear device is further configured to wirelessly communicate with the welding power source of the arc welding system. The computerized eyewear device may receive information from the welding power source and display the information on the HUD. Furthermore, the user may provide commands to the welding power source via the computerized eyewear device (e.g., via voice activation). The welding power source and the computerized eyewear device may be cooperatively configured to provide one or more of augmented indicators indicative of a user's welding technique and sequencer functionality indicative of a next weld to be made on the HUD, for example.

In another embodiment, a system is provided. The system includes a programmable processor-based subsystem of a virtual reality welding simulation system and a computerized eyewear device having a head-up display (HUD). The computerized eyewear device is configured to be worn by a user as eye glasses are worn, while the user also wears a protective welding helmet. The computerized eyewear device is further configured to wirelessly communicate with the programmable processor-based subsystem of the virtual reality welding simulation system. The computerized eyewear device may receive information from the programmable processor-based subsystem and display the information on the HUD. Furthermore, the user may provide commands to the programmable processor-based subsystem via the computerized eyewear device (e.g., via voice activation). The programmable processor-based subsystem and the computerized eyewear device may be cooperatively configured to provide one or more of virtual reality images associated with a virtual reality welding process and virtual cues and indicators associated with a virtual reality welding process on the HUD, for example.

In accordance with an embodiment, the computerized eyewear device includes a frame configured to be worn on the head of a user, the frame including a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end, the first arm being configured to be positioned over a first temple of the user with the free end disposed near a first ear of the user, wherein the bridge is adjustable for selective positioning of the brow portion relative to an eye of the user. The computerized eyewear device also includes a transparent display (the HUD) which may be affixed to the frame and may be movable with respect to the frame through rotation about a first axis that extends parallel to the first brow portion. The computerized eyewear device also includes a housing containing control and communication circuitry affixed to the frame. As an example, the computerized eyewear device may be a Google Glass™ device configured for operation with an arc welding system or a virtual reality arc welding simulation system.

Details of illustrated embodiments of the present invention will be more fully understood from the following description and drawings.

DETAILED DESCRIPTION

Figure 1:
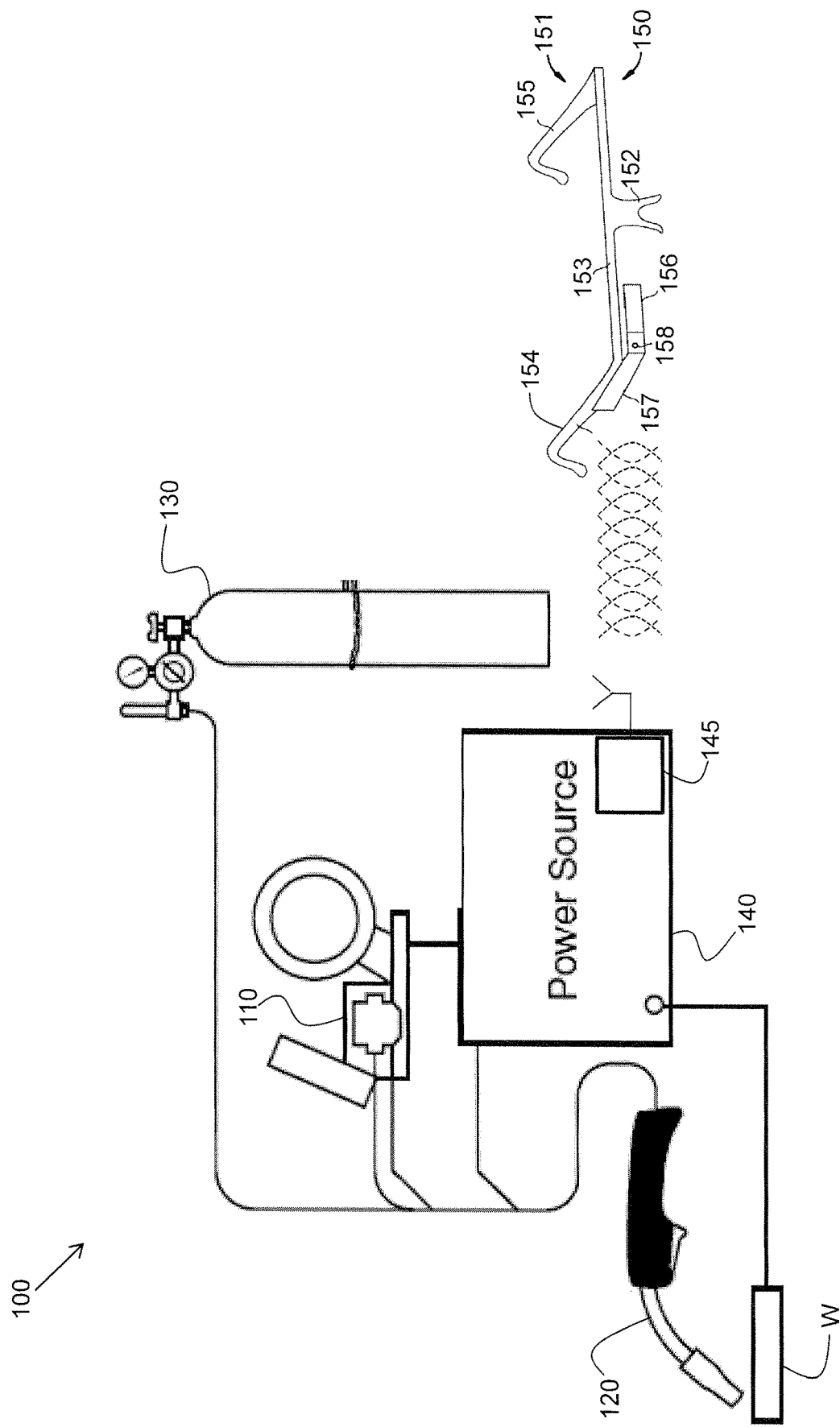
FIG. 1 illustrates a diagram of an exemplary embodiment of an arc welding system and a computerized eyewear device configured to communicate with the arc welding system.

The following are definitions of exemplary terms that may be used within the disclosure. Both singular and plural forms of all terms fall within each meaning:

"Software" or "computer program" as used herein includes, but is not limited to, one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, an application, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like.

"Computer" or "processing element" or "computerized device" as used herein includes, but is not limited to, any programmed or programmable electronic device that can store, retrieve, and process data. "Non-transitory computer-readable media" include, but are not limited to, a CD-ROM, a removable flash memory card, a hard disk drive, a magnetic tape, and a floppy disk.

"Computer memory", as used herein, refers to a storage device configured to store digital data or information which can be retrieved by a computer or processing element.

"Controller", as used herein, refers to the logic circuitry and/or processing elements and associated software or program involved in controlling a device, system, or portion of a system.

The terms "signal", "data", and "information" may be used interchangeably herein and may be in digital or analog form.

The term "welding parameter" is used broadly herein and may refer to characteristics of a portion of a welding output current waveform (e.g., amplitude, pulse width or duration, slope, electrode polarity), a welding process (e.g., a short arc welding process or a pulse welding process), wire feed speed, a modulation frequency, a welding travel speed, or some other parameter associated with real-world welding or simulated welding.

The term "head up display", as used herein, refers to a transparent display that presents information (e.g., high quality images) without requiring a user to look away from their usual viewpoints.

In one embodiment, an arc welding system is provided. The arc welding system includes a welding power source and a computerized eyewear device having a head-up display (HUD) and control and communication circuitry (CCC) operatively connected to the HUD. The computerized eyewear device is configured to be worn by a user as eye glasses are worn, while also wearing a protective welding helmet, and wirelessly communicate with the welding power source. The control and communication circuitry is configured to wirelessly receive information from the welding power source and display the information on the HUD.

In accordance with an embodiment, the computerized eyewear device includes a microphone operatively connected to the control and communication circuitry. The microphone and the control and communication circuitry are configured to receive voice-activated user command information and wirelessly transmit the voice-activated user command information to the welding power source. In accordance with an embodiment, the computerized eyewear device includes a camera operatively connected to the control and communication circuitry. The camera and the control and communication circuitry are configured to capture one or more of still pictures and moving video. In accordance with an embodiment, the control and communication circuitry is configured to access the internet through a wireless access point.

In accordance with an embodiment, the computerized eyewear device includes a frame configured to be worn on the head of a user and at least one housing affixed to the frame containing one or more of the control and communication circuitry, the microphone, and the camera. The HUD is also affixed to the frame and is movable with respect to the frame through rotation about a first axis that extends parallel to a first brow portion. Optionally, the computerized eyewear device may include at least one prescription optical lens held in place by the frame.

In accordance with an embodiment, the frame includes a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end. The first arm is configured to be positioned over a first temple of the user with the free end disposed near a first ear of the user. In accordance with an embodiment, the bridge is adjustable for selective positioning of the brow portion relative to an eye of the user.

FIG. 1 illustrates a diagram of an exemplary embodiment of an arc welding system 100 and a computerized eyewear device 150 configured to communicate with the arc welding system 100. The arc welding system 100 includes a wire feeder 110, a welding gun or tool 120, a shielding gas supply 130, and a welding power source 140. The wire feeder 110, the welding gun 120, the shielding gas supply 130, and the power source 140 are operatively connected to allow a welder to create an electric arc between a welding wire and a workpiece W to create a weld as is well known in the art.

In accordance with an embodiment, the welding power source 140 includes a switching power supply (not shown), a waveform generator (not shown), a controller (not shown), a voltage feedback circuit (not shown), a current feedback circuit (not shown), and a wireless communication circuit 145. The wire feeder 110 feeds the consumable wire welding electrode E toward the workpiece W through the welding gun (welding tool) 120 at a selected wire feed speed (WFS). The wire feeder 110, the consumable welding electrode E, and the workpiece W are not part of the welding power source 140 but may be operatively connected to the welding power source 140 via a welding output cable.

The computerized eyewear device 150 is configured to be worn by a user as eye glasses are worn, while also wearing a conventional protective welding helmet. The protective welding helmet may be a conventional welding helmet that does not have to be modified in any way to accommodate the computerized eyewear device 150. Furthermore, the computerized eyewear device 150 is configured to wirelessly communicate with the welding power source 140 via the wireless communication circuit 145 of the welding power source 140. The wireless communication circuit 145 may include a processor, computer memory, a transmitter, a receiver, and an antenna, in accordance with an embodiment.

Figure 2:
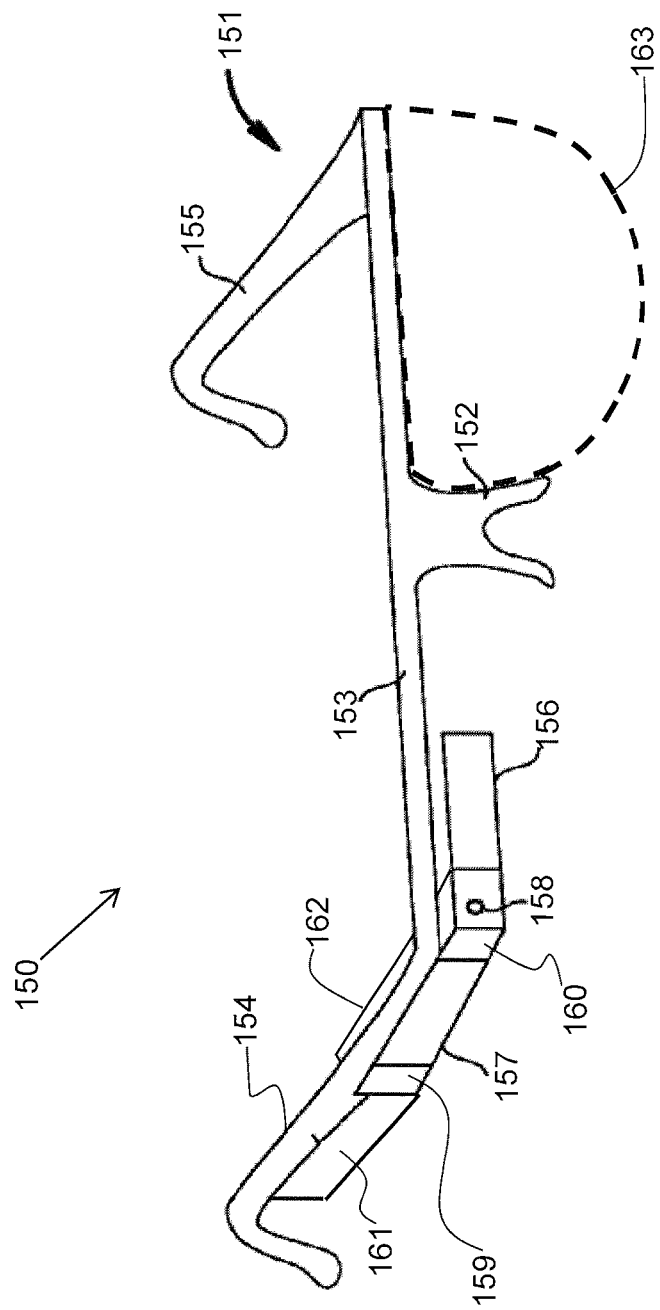
FIG. 2 illustrates a diagram of an exemplary embodiment of the computerized eyewear device of FIG. 1.

Referring now to FIG. 1 and FIG. 2, where FIG. 2 illustrates a diagram of an exemplary embodiment of the computerized eyewear device 150 of FIG. 1, the computerized eyewear device 150 includes a frame 151 configured to be worn on the head of a user. The frame 151 includes a bridge 152 configured to be supported on the nose of the user and a brow portion 153 coupled to and extending away from the bridge 152 to a first and second ends remote therefrom and configured to be positioned over the brows of the user.

The frame also includes a first arm 154 having a first end coupled to the first end of the brow portion 153 and extending to a free end, the first arm being configured to be positioned over a first temple of the user with the free end disposed near a first ear of the user. The frame 151 also includes a second arm 155 having a first end coupled to the second end of the brow portion 153 and extending to a free end, the second arm being configured to be positioned over a second temple of the user with the free end disposed near a second ear of the user. The bridge 152 may be adjustable for selective positioning of the brow portion 153 relative to the eyes of the user, in accordance with an embodiment.

The computerized eyewear device 150 includes a transparent display (e.g., a HUD) 156 affixed to the frame 151. The HUD 156 may be movable with respect to the frame 151 through rotation about a first axis that extends parallel to the brow portion 153, in accordance with an embodiment, and may be configured to display text, graphics, and images. The computerized eyewear device 150 also includes control and communication circuitry (e.g., a computer) 157 enclosed in a housing 162 and affixed to the frame 151. The control and communication circuitry 157 may include a processor and memory, for example. The memory may be coupled to the processor and store software that can be accessed and executed by the processor. The processor may be a microprocessor or a digital signal processor, for example. As an option, the computerized eyewear device 150 may include a camera 158. The HUD 156 and the control and communication circuitry 157 (and, optionally, the camera 158) are operatively connected to provide the functionality described herein. In accordance with an embodiment, the camera 158 is configured to capture still pictures and moving video. In this way, a user may record the welding scenario as viewed by the user from inside the welding helmet.

In accordance with an embodiment, the control and communication circuitry 157 provides two-way communication with the wireless communication circuit 145 of the welding power source 140. Information may be provided from the welding power source 140 to the computerized eyewear device 150 and displayed on the HUD 156. Furthermore, in accordance with an embodiment, the control and communication circuitry 157 is configured to accept voice-activated commands from a user and transmit the commands to the welding power source 140. Communication between the welding power source 140 and the computerized eyewear device 150 may be accomplished by way of, for example, Bluetooth® radio technology, communication protocols described in IEEE 802.11 (including any IEEE 802.11 revisions), cellular technology (such as GSM, CDMA, UMTS, EVDO, WiMax, or LTE), or ZigBee® technology, among other possibilities. In accordance with an embodiment, the computerized eyewear device may also include at least one optical lens 163 that matches a user's corrective visual prescription. In accordance with a further embodiment, the computerized eyewear device may be modular and attachable to normal prescription eye glasses.

Furthermore, in accordance with an embodiment, the welding power source 140 may be accessible by the computerized eyewear device 150 via the Internet. For example, the control and communication circuitry 157 may be configured to access the Internet through a wireless hot spot (e.g., a smart phone or a wireless router) and access the welding power source 140 therethrough. Alternatively, the welding power source 140 may be configured to access the Internet and provide information obtained from the Internet to the computerized eyewear device 150.

Information that may be displayed on the HUD 156 during a real-world welding scenario that may be useful to a welder may be in the form of text, an image, or a graphic. Such information may include, for example, the arc welding process, a welding tool travel angle, a welding tool travel speed, a tip-to-work distance, a wire feed speed, a welding polarity, an output voltage level, an output current level, an arc length, a dime spacing, a whip time, a puddle time, a width of weave, a weave spacing, a tolerance window, a number score, and welding sequence steps. Other information may be displayed as well, in accordance with other embodiments. For example, in an augmented mode, instructional indicators that are used in a virtual reality training environment may be superimposed over an actual weld using the HUD 156. In this manner, a welding student who trained on a virtual reality welding system can transition to a real welding scenario and have the same instructional indicators provided via the HUD. Visual cues or indicators may be displayed to the welder on the HUD of the computerized eyewear device to indicate to the welder if a particular parameter (e.g., a welding tool travel angle) is within an acceptable range or not. Such visual cues or indicators may aid in training by helping an inexperienced welder or welding student to improve his welding technique.

The acquisition of some of the information may rely on the welding tool being spatially tracked (e.g., travel angle, travel speed, tip-to-work distance). In accordance with an embodiment, the welding tool may include an accelerometer device that is operatively connected to the welding power source to provide spatial position or movement information. Other methods of tracking the welding tool are possible as well, such as magnetic tracking techniques, for example.

In accordance with an embodiment, the computerized eyewear device 150 includes a microphone 159 for receiving voice-activated commands from a user. The voice-activated commands, as initiated by a welder, that may be accommodated by the computerized eyewear device 150 in communication with the welding power source 140 may include, for example, commands to change a welding parameter such as a wire feed speed, a welding polarity, and a welding output current level. Other types of commands may be possible as well, in accordance with other embodiments.

In accordance with an embodiment, the computerized eyewear device 150 and/or the welding power source 140 may be programmed with one or more welding software applications configured to accommodate use of the computerized eyewear device 150 with the arc welding system 100. For example, an embodiment of one welding software application may provide a "good weld" recognition capability. Similar to a facial recognition capability, the "good weld" recognition capability may use the camera 158 to acquire an image of a weld created by the user, analyze the image, and provide feedback to the user on the HUD 156 as to the overall external quality of the weld. For example, the text "poor weld", "fair weld", or "good weld" may be displayed to the user. The user may have to take off his welding helmet or lift a visor on the welding helmet to acquire an image of the weld. The welding software application may reside in the computerized eyewear device 150, the welding power source 140, or a combination of both, in accordance with various embodiments.

As another example, an embodiment of a welding software application may provide a welding sequencing capability. When welding a part or assembly with many welds, it is not desirable for a welder to miss a weld. A welding software application may step a welder through the multiple welds for the part. For example, as a welder finishes a current weld on a part or assembly requiring multiple welds, the welder may give a voice command of "next weld". As a result, the welding software application may display to the welder on the HUD 156 an image or graphic (e.g., a 3D representation of the part) providing the location of the next weld to be performed. The type of weld and other information associated with the weld may also be displayed. In accordance with an embodiment where the computerized eyewear device 150 is being spatially tracked, as discussed later herein, the welding software application may display a graphic on the HUD such that graphic indicator is overlaid onto the assembly at the next location to be welded. Other types of welding software applications that operate with the computerized eyewear device are possible as well, in accordance with other embodiments.

In one embodiment, a virtual reality welding system is provided. The virtual reality welding system includes a programmable processor-based subsystem and a computerized eyewear device having a head-up display (HUD) and control and communication circuitry (CCC) operatively connected to the HUD. The computerized eyewear device is configured to be worn by a user as eye glasses are worn, and to wirelessly communicate with the programmable processor-based subsystem. The control and communication circuitry is configured to wirelessly receive information from the programmable processor-based subsystem and display the information on the HUD.

In accordance with an embodiment, the computerized eyewear device further includes a microphone operatively connected to the control and communication circuitry and configured to receive voice-activated user command information and wirelessly transmit the voice-activated user command information to the programmable processor-based subsystem. Alternatively, or in addition, the computerized eyewear device may include a touch-sensitive user interface operatively connected to the control and communication circuitry and configured to allow a user to select command information and wirelessly transmit the command information to the programmable processor-based subsystem.

In accordance with an embodiment, the computerized eyewear device includes a camera operatively connected to the control and communication circuitry. The camera and the control and communication circuitry are configured to capture one or more of still pictures and moving video. In accordance with an embodiment, the control and communication circuitry is configured to access the internet through a wireless access point.

In accordance with an embodiment, the computerized eyewear device includes a frame configured to be worn on the head of a user and at least one housing affixed to the frame containing one or more of the control and communication circuitry, the microphone, and the camera. The HUD is also affixed to the frame and is movable with respect to the frame through rotation about a first axis that extends parallel to a first brow portion. Optionally, the computerized eyewear device may include at least one prescription optical lens held in place by the frame.

In accordance with an embodiment, the frame includes a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end. The first arm is configured to be positioned over a first temple of the user with the free end disposed near a first ear of the user. In accordance with an embodiment, the bridge is adjustable for selective positioning of the brow portion relative to an eye of the user.

In accordance with an embodiment, the computerized eyewear device includes at least one motion sensing device operatively connected to the control and communication circuitry and configured to provide spatial information to the programmable processor-based subsystem as a user moves his head.

Figure 3:
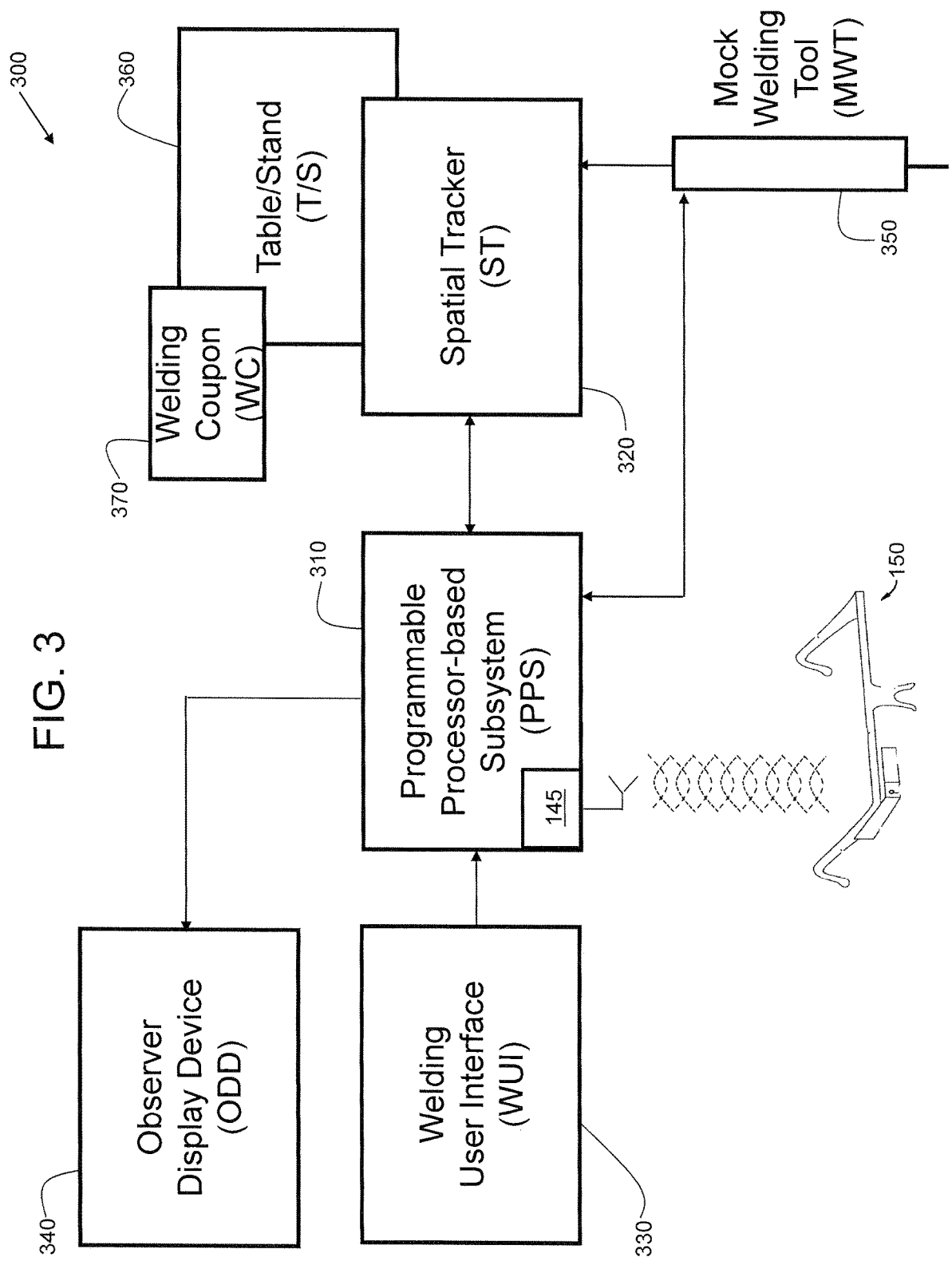
FIG. 3 illustrates a diagram of an exemplary embodiment of a virtual reality welding system and a computerized eyewear device configured to communicate with the virtual reality welding system.

FIG. 3 illustrates a diagram of an exemplary embodiment of a virtual reality arc welding system 300 and a computerized eyewear device 150 configured to communicate with the virtual reality welding system 300. The virtual reality arc welding (VRAW) system includes a programmable processor-based subsystem, a spatial tracker operatively connected to the programmable processor-based subsystem, at least one mock welding tool capable of being spatially tracked by the spatial tracker, and at least one display device operatively connected to the programmable processor-based subsystem. In accordance with an embodiment, the computerized eyewear device 150 may also be spatially tracked by the spatial tracker. The system is capable of simulating, in a virtual reality space, a weld puddle having real-time molten metal fluidity and heat dissipation characteristics. The system is also capable of displaying the simulated weld puddle on the display device in real-time.

The system 300 includes a programmable processor-based subsystem (PPS) 310. The system 300 further includes a spatial tracker (ST) 320 operatively connected to the PPS 310. The system 300 also includes a physical welding user interface (WUI) 330 operatively connected to the PPS 310 as well as the computerized eyewear device 150 in operative wireless communication with the PPS 310 via a wireless communication circuit 145 of the PPS 310. The system 300 further includes an observer display device (ODD) 340 operatively connected to the PPS 310. The system 300 also includes at least one mock welding tool (MWT) 350 operatively connected to the ST 320 and the PPS 310. The system 300 further includes a table/stand (T/S) 360 and at least one welding coupon (WC) 370 capable of being attached to the T/S 360. In accordance with an alternative embodiment of the present invention, a mock gas bottle is provided (not shown) simulating a source of shielding gas and having an adjustable flow regulator.

In accordance with an embodiment, the computerized eyewear device 150 is configured as previously described herein. However, in this embodiment, the control and communication circuitry 157 provides two-way communication with the wireless communication circuit 145 of the PPS 310. Information may be provided from the PPS 310 to the computerized eyewear device 150 and displayed on the HUD 156. Furthermore, in accordance with an embodiment, the control and communication circuitry 157 is configured to accept voice-activated commands from a user and transmit the commands to the PPS 310. Communication between the PPS 310 and the computerized eyewear device 150 may be accomplished by way of, for example, Bluetooth® radio technology, communication protocols described in IEEE 802.11 (including any IEEE 802.11 revisions), cellular technology (such as GSM, CDMA, UMTS, EVDO, WiMax, or LTE), or ZigBee® technology, among other possibilities.

Furthermore, in accordance with an embodiment, the PPS 310 may be accessible by the computerized eyewear device 150 via the Internet. For example, the control and communication circuitry 157 may be configured to access the Internet through a wireless hot spot (e.g., a smart phone or a wireless router) and access the PPS 310 therethrough. Alternatively, the PPS 310 may be configured to access the Internet and provide information obtained from the Internet to the computerized eyewear device 150.

As before, the user may wear a conventional welding helmet over the computerized eyewear device 150. However, since the welding scenario is a simulated welding scenario, the conventional welding helmet may be fitted with a transparent lens instead of a protective lens that protects against the light and other radiation emitted by a real arc. As such, the user may see through the transparent lens to view the welding coupon 370 and the mock welding tool 350, for example.

In accordance with an embodiment, the computerized eyewear device 150 is configured with an accelerometer device 160 that is operatively connected to the control and communication circuitry 157. Spatial information provided by the accelerometer device as the user moves his head is communicated to the PPS 110 and then to the spatial tracker 320. In this manner, the spatial relationship between the surrounding environment and what the user is seeing through the HUD 156 of the computerized eyewear device 150 may be correlated. As the user proceeds with the virtual welding process using the system 300, anything displayed on the HUD 156 (e.g., a virtual weld puddle) will appear overlaid onto, for example, the welding coupon 370 as the user views the welding coupon through the transparent lens of the conventional welding helmet. In accordance with other embodiments, other motion sensing devices besides that of an accelerometer device may be used. A calibration procedure may be initially performed to correlate the view of the user through the HUD to the surrounding environment, in accordance with an embodiment.

The real-time molten metal fluidity and heat dissipation characteristics of the simulated weld puddle provide real-time visual feedback to a user of the mock welding tool when displayed (e.g., on the HUD of the computerized eyewear device 150 as tracked by the spatial tracker 320), allowing the user to adjust or maintain a welding technique in real-time in response to the real-time visual feedback (i.e., helps the user learn to weld correctly). When the computerized eyewear device 150 is being spatially tracked, the weld puddle will appear at a correct location with respect to the welding coupon as viewed through the HUD.

The displayed weld puddle is representative of a weld puddle that would be formed in the real-world based on the user's welding technique and the selected welding process and parameters. By viewing a puddle (e.g., shape, color, slag, size, stacked dimes), a user can modify his technique to make a good weld and determine the type of welding being done. The shape of the puddle is responsive to the movement of the gun or stick.

The term "real-time", as used herein with respect to a virtual reality or simulated environment, means perceiving and experiencing in time in a virtual or simulated environment in the same way that a user would perceive and experience in a real-world welding scenario. Furthermore, the weld puddle is responsive to the effects of the physical environment including gravity, allowing a user to realistically practice welding in various positions including overhead welding and various pipe welding angles (e.g., 1G, 2G, 5G, 6G).

Information that may be useful to a welding student to display on the HUD 156 during a virtual or simulated welding scenario may be in the form of text, an image, or a graphic. Such information may include, for example, the arc welding process, a welding tool travel angle, a welding tool travel speed, a tip-to-work distance, a set wire feed speed, a set welding polarity, a simulated output voltage level, a set output current level, a simulated arc length, a dime spacing, a whip time, a puddle time, a width of weave, a weave spacing, a tolerance window, a number score, and welding sequence steps. Other information may be displayed as well, in accordance with other embodiments.

In accordance with an embodiment, the computerized eyewear device 150 includes a microphone 159 that is operatively connected to the control and communication circuitry 157 for receiving voice-activated commands from a user. The voice-activated commands, as initiated by a welder, that may be accommodated by the computerized eyewear device 150 in communication with the PPS 310 may include, for example, commands to change a welding parameter such as a simulated wire feed speed, a simulated welding polarity, and a simulated welding output current level. Other types of commands may be possible as well, in accordance with other embodiments.

In accordance with an embodiment, the computerized eyewear device 150 and/or the PPS 310 may be programmed with one or more welding training software applications configured to accommodate use of the computerized eyewear device 150 with the virtual reality arc welding system 300. For example, an embodiment of one welding software application may provide a "good weld" recognition capability. Similar to a facial recognition capability, the "good weld" recognition capability may use an image of a simulated weld created by the user, analyze the image, and provide feedback to the user on the HUD 156 as to the overall external quality of the weld. For example, the text "poor weld", "fair weld", or "good weld" may be displayed to the user. The welding software application may reside in the computerized eyewear device 150, the PPS 310, or a combination of both, in accordance with various embodiments.

As another example, an embodiment of a welding software application may provide a welding sequencing capability. As a welder finishes a current simulated weld on a welding coupon requiring multiple welds, the welder may give a voice command of "next weld". As a result, the welding software application may display to the welder on the HUD 156 an image or graphic providing the location of the next weld to be performed. The type of weld and other information associated with the weld may also be displayed. In accordance with an embodiment where the computerized eyewear device 150 is being spatially tracked, as discussed herein, the welding software application may display a graphic on the HUD such that the graphic is overlaid onto the welding coupon at the next location to be welded. Other types of welding software applications that operate with the computerized eyewear device are possible as well, in accordance with other embodiments.

The computerized eyewear device 150 may be configured to be used with other welding simulation systems in accordance with other embodiments. For example, welding simulations performed on a personal computer (PC) or a tablet computer may be communicatively and functionally integrated with the computerized eyewear device 150 to aid a welding student in learning how to weld. In some simulated and/or virtual welding environments, a welding student may not wear a welding helmet of any kind. Instead, the computerized eyewear device may be the only head gear worn. One optional embodiment of the computerized eyewear device may provide a touch-sensitive user interface (TSUI) 161 which the welding student can use instead of or in addition to voice-activated commands. Such a TSUI would be accessible to the welding student when not wearing a welding helmet, for example. In accordance with an embodiment, the TSUI 161 is operatively connected to the control and communication circuitry 157.

In summary, systems and methods to aid a welder or welding student are provided. A system may include a real-world arc welding system or a virtual reality arc welding system along with a computerized eyewear device having a head-up display (HUD). The computerized eyewear device may be worn by a user under a conventional welding helmet as eye glasses are worn and may wirelessly communicate with a welding power source of a real-world arc welding system or a programmable processor-based subsystem of a virtual reality arc welding system.

In appended claims, the terms "including" and "having" are used as the plain language equivalents of the term "comprising"; the term "in which" is equivalent to "wherein." Moreover, in appended claims, the terms "first," "second," "third," "upper," "lower," "bottom," "top," etc. are used merely as labels, and are not intended to impose numerical or positional requirements on their objects. Further, the limitations of the appended claims are not written in means-plus-function format and are not intended to be interpreted based on 35 U.S.C. § 112, sixth paragraph, unless and until such claim limitations expressly use the phrase "means for" followed by a statement of function void of further structure. As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. Moreover, certain embodiments may be shown as having like or similar elements, however, this is merely for illustration purposes, and such embodiments need not necessarily have the same elements unless specified in the claims.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

This written description uses examples to disclose the invention, including the best mode, and also to enable one of ordinary skill in the art to practice the invention, including making and using any devices or systems and performing any incorporated methods. The scope of the invention is defined by the claims, and may include other examples that occur to one of ordinary skill in the art. Such other examples are intended to be within the scope of the claims if they have structural elements that do not differentiate from the literal language of the claims, or if they include equivalent structural elements with insubstantial differences from the literal language of the claims.

While the invention of the present application has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiments disclosed, but that the invention will include all embodiments falling within the scope of the appended claims.

What is claimed is:

1. An arc welding system, comprising:
a welding power source; and
a computerized eyewear device configured to be worn by a user as eye glasses are worn, while also wearing a protective welding helmet, wherein the computerized eyewear device includes a transparent head-up display (HUD), which displays an augmented reality image to the user performing a welding operation with the welding power source, a wireless communication interface, a processor, and a memory storing computer-executable instructions, wherein the computer-executable instructions configure the computerized eyewear device to:
communicate with the welding power source via the wireless communication interface,
display information related to the welding power source on the HUD as part of the augmented reality image, and
provide weld sequence support to the user to guide the user through a sequence of two or more welds associated with a workpiece through incorporation of support information in the augmented reality image displayed on the HUD, wherein, upon completion of a weld of the sequence, the augmented reality image displays the support information indicating a next weld of the sequence to be performed on the workpiece.

2. The system of claim 1, wherein the information related to the welding power source includes at least one welding parameter associated with the welding operation.

3. The system of claim 1, wherein the computerized eyewear device further includes a microphone configured to receive voice-activated user command information and wirelessly transmit the voice-activated user command information to the welding power source.

4. The system of claim 1, wherein the computerized eyewear device further includes a camera configured to capture one or more of still pictures and moving video.

5. The system of claim 1, wherein the computerized eyewear device is configured to access the internet through a wireless access point.

6. The system of claim 1, wherein the computerized eyewear device further includes a frame configured to be worn on the head of a user.

7. The system of claim 6, wherein the computerized eyewear device further includes at least one housing affixed to the frame containing one or more of the the processor, the wireless communication interface, the memory, a microphone, and a camera.

8. The system of claim 6, wherein the HUD is affixed to the frame and is movable with respect to the frame through rotation about a first axis that extends parallel to a brow portion of the frame.

9. The system of claim 6, wherein the computerized eyewear device further includes at least one prescription optical lens held in place by the frame.

10. The system of claim 6, wherein the frame includes a bridge configured to be supported on the nose of the user, a brow portion coupled to and extending away from the bridge to a first end remote therefrom and configured to be positioned over a first side of a brow of the user, and a first arm having a first end coupled to the first end of the brow portion and extending to a free end, the first arm being configured to be positioned over a first temple of the user with the free end disposed near a first ear of the user.

11. The system of claim 10, wherein the bridge is adjustable for selective positioning of the brow portion relative to an eye of the user.

12. The system of claim 2, wherein the augmented reality image displayed on the HUD depicts an indication of whether the at least one welding parameter is within an acceptable range.

* * * * *